United States Patent [19]

Anderson et al.

[11] Patent Number: 4,855,496
[45] Date of Patent: Aug. 8, 1989

[54] PROCESS FOR THE PREPARATION OF FORMIC ACID

[75] Inventors: Jeffrey J. Anderson, Sproatley; David J. Drury, Strawberry Hill; John E. Hamlin, Hull; Alexander G. Kent, Beverley, all of England

[73] Assignee: BP Chemicals Limited, London, England

[21] Appl. No.: 864,725

[22] PCT Filed: Sep. 26, 1985

[86] PCT No.: PCT/GB85/00443
§ 371 Date: Apr. 30, 1986
§ 102(e) Date: Apr. 30, 1986

[87] PCT Pub. No.: WO86/02066
PCT Pub. Date: Apr. 10, 1986

[30] Foreign Application Priority Data

Sep. 29, 1984 [GB] United Kingdom ............... 84/24672

[51] Int. Cl.$^4$ ..................... C07C 51/097; C07C 53/02
[52] U.S. Cl. .................................................. 562/609
[58] Field of Search ...................... 562/609; 260/501.1

[56] References Cited

U.S. PATENT DOCUMENTS 4,218,568  8/1980  Hohenschutz et al. ........ 562/609 X
4,474,959  10/1984  Drury et al. .................... 562/609 X

FOREIGN PATENT DOCUMENTS 95321  11/1983  European Pat. Off. ............ 562/609
126524  9/1984  European Pat. Off. ............ 562/609

OTHER PUBLICATIONS

Anderson et al., Australian Patent Abstract, vol. 54, No. 35, Sep. 20, 1984.

Primary Examiner—Werren B. Lone
Attorney, Agent, or Firm—Brooks, Haidt, Haffner & Delahunty

[57] ABSTRACT

An integrated process for the production of formic acid from carbon dioxide and hydrogen. The process comprises for example, a reactor in which the formate salt of a nitrogenous base is produced together with subsequent purification and formic acid recovery stages. In the process described formic acid is recovered from the formate salt by using a base interchange reaction in which there is generated a thermally decomposable formate salt of a high boiling base. The high boiling base can be for example an imidazole and the nitrogenous base can be triethylamine.

11 Claims, 1 Drawing Sheet

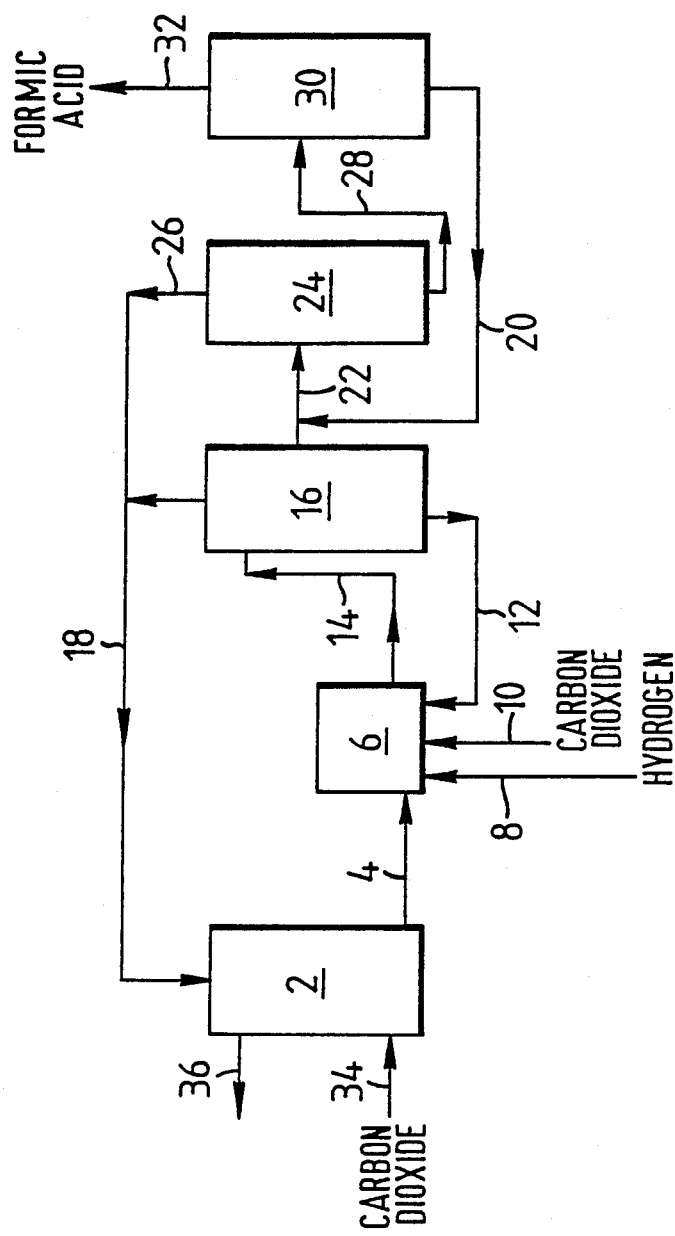

PROCESS FOR THE PREPARATION OF FORMIC ACID

The present invention provides a process for the production of formic acid from carbon dioxide and hydrogen using an integrated series of process steps.

Our European patent application Nos. 0095321 and 84301772.4 respectively describe a method for the production of a trialkylammonium formate from a tertiary amine, carbon dioxide and hydrogen and a method for converting the trialkylammonium formate into another formate salt which is thermally decomposable to formic acid.

An integrated process has now been devised which allows formic acid to be prepared from carbon dioxide and hydrogen feedstocks only.

Accordingly, the present invention provides an integrated process for the production of formic acid from carbon dioxide and hydrogen characterised in that (a) in a first stage a nitrogenous base, carbon dioxide and hydrogen are reacted together in the presence of a catalyst to produce a formate salt of the nitrogenous base.
(b) in a second stage the catalyst is removed from the formate salt of the nitrogenous base and any low boilers and recycled to the first stage;
(c) in a third stage the formate salt of the nitrogenous base is recovered from the low boilers.
(d) in a fourth stage the formate salt of the nitrogenous base is reacted with a base having a high boiling point to produce the nitrogenous base and the formate salt of the base having a high boiling point.
(e) in a fifth stage the formate salt of the base having a high boiling point is decomposed to the higher boiling base and formic acid.

By the term nitrogenous base is meant a nitrogenous base containing a tertiary nitrogen atom. The nitrogenous base containing a tertiary nitrogen atom maay suitably be of formula

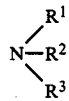

or of formula:

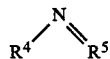

wherein in the formulae, $R^1$, $R^2$ and $R^3$, which may be the same or different, are hydrocarbyl groups or substituted hydrocarbyl groups or any two or all of $R^1$, $R^2$ and $R^3$ may form part of a ring, $R^4$ is a hydrocarbyl group or substituted hydrocarbyl group and $R^5$ is a divalent organic group or $R^4$ and $R^5$ may form part of a ring. Suitably the hydrocarbyl group is an aliphatic, cycloaliphatic, aryl, or alkaryl group. Substituted hydrocarbyl groups may contain for example nitrogen or oxygen. Preferably the organic base is a trialkylamine, even more preferably a lower trialkylamine, for example a $C_1$ to $C_{10}$ trialkylamine. Examples of suitable trialkylamines are trimethylamine, triethylamine, tripropylamine and tributylamine. Examples of other nitrogenous bases which may be employed are 1,8-diazabicyclo[5.4.0]undec-7-ene (DBU) and 1,4-diazabicyclo[2.2.2]octane (DABCO), pyridines and picolines. Mixtures of nitrogenous bases may also be used.

The formate salt produced in the first stage of the process corresponds to the nitrogenous base used in this stage. Thus using triethylamine the product is triethylammonium formate.

As regards the base having a high boiling point, this is suitably also a nitrogenous base and is selected so that (1) it is weaker than the nitrogenous base used in the first stage of the process.
(2) its formate salt is thermally decomposable at a temperature higher than the boiling point of the nitrogenous base used in the first stage of the process, and
(3) it is less volatile than the nitrogenous base used in the first stage of the process.

It will be seen from these criteria that the exact choice of such a base will depend upon which nitrogenous base is used in the first stage of the process.

Preferably the second base has a pKa in the range 4.0 to 9.0 and is an imidazole of the general formula:

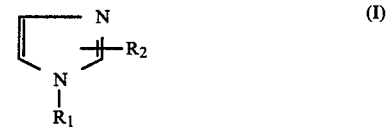

where $R_1$ is a monovalent hydrocarbon group containing 1 to 12 carbon atoms and $R_2$ is a hydrogen atom or an $R_1$ group, the total number of carbon atoms and $R_1$ and $R_2$ conveniently being not more than 20 and preferably from 4 to 12.

Suitable hydrocarbon radicals on the imidazole derivatives (I) are, in general, alkyl groups of 1 to 8 carbon atoms, cyclopentyl, cyclohexyl, phenyl and methylphenyl groups. Amongst the above, imidazole derivatives where $R^1$ is n-1-alkyl of 4 to 10 carbon atoms and $R^2$ is hydrogen or methyl are particularly suitable. Examples of such compounds are 1-(n-1-butyl)-imidazole (pKa 5.9), 1-(n-1-pentyl)-imidazole (pKa 5.9), 1-(n-1-decyl)-imidazole (pKa 5.75), 1-(n-1-butyl)-2-methylimidazole (pKa 7.0) and 1-(n-1-pentyl)-2-methylimidazole (pKa 6.85).

In addition to imidazoles, quinoline and other heterocyclic nitrogenous bases can be used.

For a definition of the pKa values, which are a measure of the base strength, reference may be made, for example to Landoldt-Bornstein, 6th edition, 7th part volume II, page 900 et seq.

As catalyst there is used a compound of a Group VIII transition metal, which is either iron, nickel, ruthenium, rhodium, palladium, iridium or platinum. Suitably the metal is ruthenium or thodium and is preferably ruthenium. Mixtures of compounds of different transition metals may also be used if so desired. The metal or metals may be added in any convenient form which is soluble in the reaction mixture. Thus the metal or metals may be added in the form of a simple salt, for example a halide, or in the form of a complex, for example a hydride complex. Examples of suitable ruthenium compounds which may be employed as catalyst are $RuCl_2(PPh_3)_3$, $RuH_2(PPh_3)_4$, $RuHCl(PPh_3)_4$, $RuCl_3.3H_2O$, $[Ru(CO)_2Cl_2]_n$, $[Ru(CO)_2I_2]_2$, [p-cymene)-$RuCl_2]_2$, [(hexamethylbenzene)$RuCl_2]_2$ and [(hexamethylbenzene)$Ru_2(OH)_3Cl$]. Suitably the catalyst concentration may be in the range 50 to 5000, preferably from 250 to 1000 parts per million by weight (as the metal in the complex).

The operation of the process is now described with reference to the FIGURE, which illustrates a schematic example of a plant using the process.

A recycle stream containing the nitrogenous base and water is fed via line (4) to the first stage, reactor (6), along with three other streams, (a) a hydrogen stream (via line (8)), (b) a carbon dioxide stream (via line (10)) and (c) a catalyst stream (via line (12)). The catalyst stream preferably comprises a solution of the catalyst in a high boiling point solvent.

It is important that the high boiling solvent is selected so that
(i) the catalyst is soluble in the recycle stream (12) (ie the solvent acts as a catalyst carrier),
(ii) the solvent does not adversely affect the activity of the catalyst in the reaction stage (6) and,
(iii) the nitrogenous base formate produced in the first stage can readily be separated from the solvent.

The high boiling solvent may be for example either one or more alcohols.

Example of solvents include, diethylene glycol, tetraethylene glycol, polyethylene glycol, 1-phenyl-1-propanol and 3-phenyl-1-propanol. Sulpholanes can also be used. It is preferred to use as solvent either tetraethylene glycol or polyethylene glycol (average MW 400). In the reactor (6) it is preferable though not essential also to have some water present as this increases the reaction rate.

The reactor (6) is suitably operated at a temperature in the range from 20° to 200°, preferably from 60° to 130° C.

The carbon dioxide may either be carbon dioxide itself, which is widely available on an industrial scale, or a carbon dioxide obtained from a carbonate or a bicarbonate sources. Alternatives carbonates or bicarbs can be used directly. Carbon dioxide may be used as a gas or as a liquid or as a solid. Using carbon dioxide gas as the source of carbon dioxide it it preferred to use partial pressures of carbon dioxide and hydrogen which are as high as is practicable and economic. The use of high partial pressures of hydrogen is desirable because the reaction rate and yield of the formate salt increase as the partial pressure increases. The partial pressure of carbon dioxide is less critical but suitably the carbon dioxide partial pressure may be up to 60 bar and the hydrogen partial pressure up to 250 bar.

Conveniently the partial pressure of carbon dioxide is from 10 to 50 bar and that of hydrogen from 10 to 150 bar. The ratio of the partial pressure of hydrogen to that of carbon dioxide in reactor (6) is preferably at least 1:1 more preferably at least 1.5:1.

The product from the first stage reactor comprises unreacted materials, the formate salt of the nitrogenous base and catalyst in a water/high boiling solvent mixture. This product from the first stage reactor (6) is fed via line (14) to a second stage (16) where the catalyst and the high boiling solvent are removed.

The second stage (16) may suitably comprise:
(a) an evaporator, where (i) the catalyst and the high boiling solvent are separated and recycled to the first stage reactor (6) via line (12) and (ii) the gaseous components are separated and recycled via line (18) followed by
(b) a unit for the separation of unreacted nitrogenous base and water (also for recycle via line (18)) from the formate salt of the nitrogenous base. This may take the form of (i) a decanter (to separate any aqueous and organic phases) or (ii) a distillation column. The formate salt of the nitrogenous base is removed from the second stage via line (22).

Alternatively the second stage (16) can be a distillation tower where the gaseous componets i.e. carbon dioxide, hydrogen and the low boilers, i.e. the nitrogenous base and some water are removed overhead and the intermediate boilers i.e. the formate salt of the nitrogenous base and some water are removed at an intermediate point in the column via line (22). The gaseous products and low boilers are recycled via line (18) while the non volatile catalyst/high boiling solvent mixtures recycled as a liquid to the first stage reactor (6) via line (12).

After the second stage, the (aqueous) solution of the formate salt of the nitrogenous base, is fed via line (22) to the third stage (24) which can consist for example of a reaction kettle with a distillation column mounted on top. The formate salt of the nitrogenous base is fed to the column along with an appropriate base having a high boiling point fed via line (20). By maintaining the column at high temperature a base interchange reaction is set up with the result that the nitrogenous base is liberated and the formate salt of the base having a high boiling point is formed. The nitrogenous base is removed overhead in the distillation column and recycled via line (26) thereby driving the base interchange reaction to completion. The product, which comprises a solution of the formate salt of the base having a high boiling point is removed from the kettle via line (28) and fed to the fourth and final stage (30).

The rate of the base interchange reaction in the third stage is increased by using high temperatures e.g. one greater than the boiling point of the nitrogenous base and subatmospheric pressure. It is preferred therefore to use as high a temperature as possible, without producing undesirable decomposition products, and to use as low a distillation pressure as is economically practicable.

In the fourth stage (30) the feed from line (28) is heated to a temperature at which the formate salt of the base having a high boiling point decomposes to formic acid and the base having a high boiling point. It is preferable to use subatmospheric pressure to reduce the formation of side products. The formic acid is removed overhead via line (32) and can be further purified if desired while the remaining solution of the high boiling base is recycled to line (22) via line (20).

The recycle components are fed via line (18) and line (26) to a gas scrubber (2). The gas scrubber is an optical feature. Inside the gas scrubber (2) the recycle components are contacted with carbon dioxide in the form of a gaseous stream fed via line (34) and vented via line (36). The gaseous stream of carbon dioxide can be, for example
(1) low value carbon dioxide from another plant such as a fermentation process or boiler flue.
(2) a carbon dioxide containing off-gas from another part of the process,
(3) carbon dioxide derived from a unit specifically designed for the manufacture of carbon dioxide.
(4) carbon dioxide produced by a plant which makes $CO_2$ as a byproduct.
(5) carbon dioxide from a gas field.

In the gas scrubber (2), some or all of the carbon dioxide present in the gaseous stream is removed and solubilised in the recycle components.

During the solubilisation of the gas, the carbon dioxide reacts with the nitrogenous base and water present in the recycle components to produce at least in part, bicarbonate of the nitrogenous base. This bicarbonate provides a useful method of carrying carbon dioxide via line (4) to the first stage reactor (6) where it is also converted to the corresponding formate. The invention is illustrated by the following Examples.

EXAMPLE 1

Production of Triethylammonium Formate

A liquid feed of composition 21.9% w/w triethylamine, 76.4% w/w tetraethylene glycol with 1.7% w/w water containing ruthenium catalyst (500 parts per million in ruthenium) was introduced into a one liter stirred stainless steel reactor at a rate of 2000 ml/hour. Liquid carbon dioxide was also introduced at 232 g/hour and hydrogen fed to keep the pressure of the reactor at 100 bar; a liquid product was taken from the reactor in order to keep the reactor inventory as near to 500 g as possible. A 2.67 hour mass accountability study was carried out following a 5.0 hour prerun to establish steady operating conditions. During the balance period, 5199 g feed were introduced and 5774 g of liquid product obtained. The reactor productivity was estimated as 6.2 moles/Kg reactor charge/hour. The reactor product contained triethylammonium formate (20.9% w/w as a 1:1 adduct).

EXAMPLE 2

Base Interchange Reaction

A feed of composition 63.4% w/w 1-n-butylimidazole, 34.8% w/w triethylammonium formate ([NEt$_3$][HCO$_2$H]$_2$), 1.8% w/w water was introduced into a distillation column (set for total take-off) at a kettle temperature of 178° C. and atmospheric pressure. During a mass accountability study following a pre-run to achieve steady operating conditions, 1940.9 g of feed were introduced, and 858.2 and 160.7 g of base and overhead products obtained. Analysis of the feed and products showed the following respective % w/w's of triethylamine (present in the feed as the formate) and 1-n-butylimidazole (present in the product as the formate). Feed 18.7 and 63.4, Base product 2.9 and 76.2 and Overhead product 91.0 and 0.1.

EXAMPLE 3

Base Formate Decomposition

A feed of composition 93.5% w/w 1-n-butylimidazolium formate, 4.7% w/w 1-n-butylimidazole and 1.8% w/w water was introduced into a distillation column at 185° C. and 150 mm Hg. A reflux ratio of 0.5 was employed. During a mass accountability study of 1 hour, following a pre-run to achieve steady operating conditions, 436.6. g of feed were introduced and 382.0 and 71.7 g of base and overhead products obtained. The base and overhead products contained respectively 17.5 w/w formic acid (present as 1-n-butylimidazolium formate) and 88.0% w/w formic acid.

We claim:

1. An integrated process for the production of formic acid from carbon dioxide and hydrogen characterised in that
   (a) in a first stage a first nitrogenous base, carbon dioxide and hydrogen are reacted together in the presence of a Group VIII transition metal catalyst and in the presence of a high boiling solvent selected from the group consisting of, polyethylene glycol, 1-phenyl-1-propanol, 3-phenyl-1-propanol and sulpholane, to produce a formate salt of the first nitrogenous base;
   said first nitrogenous base containing a tertiary nitrogen atom selected from nitrogenous bases of the formulae:

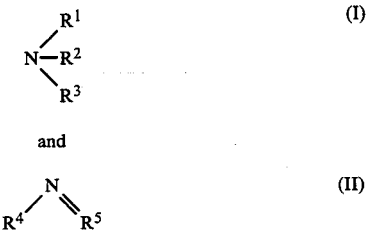

wherein in the formulae, R$^1$, R$^2$ and R$^3$, may be the same or different, are hydrocarbyl groups or substituted hydrocarbyl groups containing oxygen or nitrogen or any two of R$^1$, R$^2$ and R$^3$ may form part of a ring, R$^4$ and R$^5$ form part of a ring;
   (b) in a second stage the catalyst is removed from the formate salt of the first nitrogenous base and any low boilers and recycled to the first stage, wherein in the second state the catalyst is removed and recycled as a solution in the high boiling solvent;
   (c) in a third stage the formate salt of the first nitrogenous base is recovered from the low boilers;
   (d) in a fourth stage the formate salt of the first nitrogenous base is reacted with a second base which is (i) weaker than the first nitrogenous base used in the first stage, (ii) in the form of its formate salt is thermally decomposable at a temperature higher than the boiling point of the first nitrogenous base used in the first stage, and (iii) is less volatile than the first nitrogenous base used in the first stage, to produce the first nitrogenous base and the formate salt of the second base;
   (e) in a fifth stage the formate salt of the second base is thermally decomposed to the second base and formic acid.

2. An integrated process as claimed in claim 1 characterised in that the catalyst is a ruthenium catalyst.

3. An integrated process as claimed in claim 1 characterised in that the nitrogenous base is a C$_1$ to C$_{10}$ trialkylamine.

4. An integrated process as claimed in claim 1 characterised in that the second base is an imidazole or a quinoline.

5. An integrated process as claimed in claim 1 characterised in that the fourth stage is carried out at temperature above the boiling point of the nitrogenous base and subatmospheric pressure.

6. An integrated process as claimed in claim 1 characterised in that the fifth stage is carried out at subatmospheric pressure.

7. An integrated process as claimed in claim 1, characterised in that the high boiling solvent is tetraethylene glycol.

8. An integrated process as claimed in claim 1, characterised in that the high boiling solvent is polyethylene glycol.

9. An integrated process for the production of formic acid from carbon dioxide and hydrogen characterised in that
(a) in a first stage a first nitrogenous base, carbon dioxide and hydrogen are reacted together in the presence of a Group VIII transition metal catalyst and in the presence of a high boiling solvent selected from alcohols and sulpholanes to produce a formate salt of the first nitrogenous base;

said high boiling solvent being one capable of functioning as a catalyst carrier, which does not adversely affect the activity of the catalyst and is capable of separation from the first nitrogenous base formate produced in the first stage;

said first nitrogenous base containing a tertiary nitrogen atom selected from nitrogenous bases of the formulae:

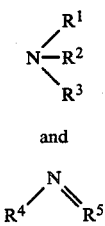

and wherein in the formulae, $R^1$, $R^2$ and $R^3$, may be the same or different, are hydrocarbyl groups or substituted hydrocarbyl groups containing oxygen or nitrogen or any two of $R^1$, $R^2$ and $R^3$ may form part of a ring, $R^4$ and $R^5$ form part of a ring;

(b) in a second stage the catalyst is removed from the formate salt of the first nitrogenous base and any low boilers and recycled to the first stage, wherein in the second stage the catalyst is removed and recycled as a solution in the high boiling solvent;

(c) in a third stage the formate salt of the first nitrogenous base is recovered from the low boilers;

(d) in a fourth stage the formate salt of the first nitrogenous base is reacted with a second base which is (i) weaker than the first nitrogenous base used in the first stage, (ii) in the form of its formate salt is thermally decomposable at a temperature higher than the boiling point of the first nitrogenous base used in the first stage, and (iii) is less volatile than the first nitrogenous base used in the first stage, to produce the first nitrogenous base and the formate salt of the second base;

(e) in a fifth stage the formate salt of the second base is thermally decomposed to the second base and formic acid.

10. A process according to claim 9 wherein the high boiling solvent is an alcohol selected from tetraethylene glycol, polyethylene glycols, 1-phenyl-1-propanol and 3-phenyl-1-propanol.

11. A process according to claim 10 wherein the high boiling solvent is either tetraethylene glycol or a polyethylene glycol having an average molecular weight of 400.

* * * * *

UNITED STATES PATENT AND TRADEMARK OFFICE
CERTIFICATE OF CORRECTION

PATENT NO. : 4,855,496
DATED : August 8, 1989
INVENTOR(S) : JEFFREY J. ANDERSON, et al It is certified that error appears in the above-identified patent and that said Letters Patent is hereby corrected as shown below:

Col. 1, line 38, should read "..nitrogen atom ma_y.."

Col. 2, line 55, should read "..ruthenium or _rhodium.."

Col. 6, line 29, change "state" to ..stage..

Claim 10, lines 2 and 3, strike "tetraethylene glycol".

Signed and Sealed this

Fourteenth Day of August, 1990

Attest:

HARRY F. MANBECK, JR.

*Attesting Officer*   *Commissioner of Patents and Trademarks*